(12) United States Patent
Muraishi

(10) Patent No.: US 7,550,288 B2
(45) Date of Patent: Jun. 23, 2009

(54) REACTION METHOD WITH USE OF BIOCHEMICAL ANALYSIS UNIT

(75) Inventor: Katsuaki Muraishi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 275 days.

(21) Appl. No.: 10/950,486

(22) Filed: Sep. 28, 2004

(65) Prior Publication Data

US 2005/0070029 A1    Mar. 31, 2005

(30) Foreign Application Priority Data

Sep. 30, 2003    (JP)    ............... 2003-341202

(51) Int. Cl.
*C12M 1/34*    (2006.01)
(52) U.S. Cl. .............. 435/287.2; 436/548; 436/524; 436/528; 435/283.1; 435/287.7; 435/287.8; 435/288.3; 435/288.4; 422/50; 422/61; 422/68.1; 422/82.05
(58) Field of Classification Search .......... 436/518, 436/524, 528; 435/283.1, 287.2, 287.7, 287.8, 435/288.3, 288.4, 288.7; 422/50, 61, 68.1, 422/82.05
See application file for complete search history.

(56) References Cited

U.S. PATENT DOCUMENTS

| | | | | |
|---|---|---|---|---|
| 4,427,415 A | | 1/1984 | Cleveland | |
| 5,478,751 A | * | 12/1995 | Oosta et al. | ............... 436/165 |
| 5,726,010 A | * | 3/1998 | Clark | ............... 435/5 |
| 5,792,425 A | * | 8/1998 | Clark et al. | ............... 422/101 |
| 2002/0094533 A1 | * | 7/2002 | Hess et al. | ............... 435/6 |
| 2003/0022246 A1 | * | 1/2003 | Ogura et al. | ............... 435/7.9 |
| 2003/0045002 A1 | | 3/2003 | Muraishi | |
| 2003/0148402 A1 | * | 8/2003 | Amano et al. | ............... 435/7.9 |
| 2004/0115707 A1 | | 6/2004 | Amano | |

FOREIGN PATENT DOCUMENTS

| | | |
|---|---|---|
| EP | 1 333 283 A2 | 8/2003 |
| JP | 2002-355036 A | 12/2002 |
| WO | WO 01/45843 A2 | 6/2001 |

* cited by examiner

*Primary Examiner*—Bao-Thuy L Nguyen
*Assistant Examiner*—Melanie J. Yu
(74) *Attorney, Agent, or Firm*—Sughrue Mion, PLLC

(57) ABSTRACT

A biochemical analysis unit has a flow-through area in which plural spot areas are arranged, and probes are spotted onto the spot areas. The biochemical analysis unit is set into a chamber of a reaction vessel. A reaction solution containing a target is supplied through an inlet into the chamber. A flow rate is adjusted such that the pressure loss may be 80 kPa when the reaction solution flows through the flow-through area. When the pressure loss is increased, the reaction solution flows through the flow-through area after equivalently spreading into a lower side of the chamber. Thus the flowing speed is decreased.

5 Claims, 6 Drawing Sheets

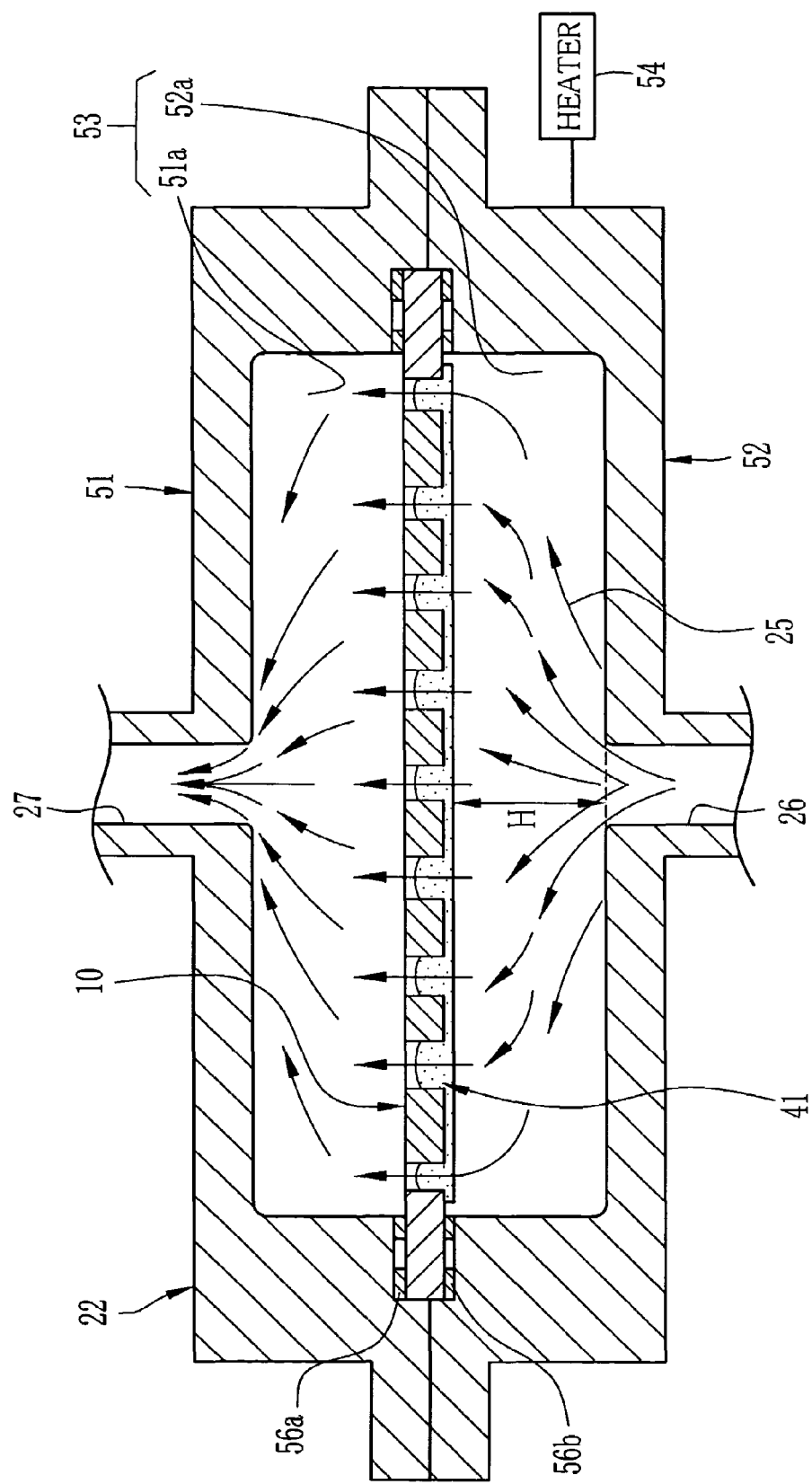

REACTION METHOD WITH USE OF BIOCHEMICAL ANALYSIS UNIT

BACKGROUND OF THE INVENTION

1. Field of the Invention

The present invention relates to a reaction method with use of a biochemical analysis unit which is used for base sequence analysis of DNA and the like.

2. Description Related to the Prior Art

In order to make a biochemical analysis for base sequence of substances derived from living organism (for example DNA), a biochemical analysis unit is used. In order to obtain the biochemical analysis unit, minute through holes are formed in the substrate, and porous materials and the like are pressed into each through hole to form a spot area. Thus, the spot areas are arranged on the substrate, and therefore the biochemical analysis unit is called also microarray. A method of biochemical analysis, in which the biochemical analysis unit is used, includes a spotting process, a reaction process, a data reading process, and a data analysis process. In the spotting process, a specific binding substance as a reagent (hereinafter probe) is spotted and fixed in the spot areas on the biochemical analysis unit. In the reaction process, a specific binding substance as a test body (hereinafter target) is penetrated into the spot areas, and the specific binding (the biding between the probe and the target) is made. In the data reading process a biochemical analysis data is read out from the biochemical analysis unit as a result of the specific binding reaction in each spot area. In the data analysis process, the read out analysis data is analyzed in the personal computer and the like. (see, Japanese Patent Laid-Open Publication No. 2002-355036).

Since the probe is a reagent for searching the information of expression, the molecular structure (for example base sequence, composition and the like) of the used probe is already known. As the probe, there are substances derived from living organism (such as hormones, tumor markers, enzymes, antibodies, antigens, abzymes, receptors, other proteins, ligand, nucleic acids, cDNA, DNA, mRNA, and the like, which are extracted and isolated from the living organism), and products obtained by performing the chemical treatments or the chemical modifications of the substances derived from living organism.

When the base sequence is searched, several sorts of the probes are fixed in respective spot areas of the biochemical analysis unit in the spotting process. Then in the reaction process, a solution in which the target is dissolved to a solvent is penetrated in the spot areas, and the specific binding of the target and the probe having a complemental relation to the target is made. In order to detect the specific binding, the reaction solution contains for example labeling substances. As the labeling substances to be used, there are radioactive substances which generate a radial ray. After the specific binding is made, the biochemical analysis unit is cleaned to remove the reaction solution on other areas than spot areas.

In the spot area in which the specific binding is made, the labeling substances remain. Thus the specific binding is detected based on the radial ray from the labeling substance in the data reading process. As a device for reading data, a scanner is used. However, in an image pickup apparatus for reading the optical information, the radial image cannot be directly picked up. Accordingly, when the radioactive substances are used as the labeling substances, a stimulable phosphor sheet is used. In the stimulable phosphor sheet, the radioactive energy in the spot area in which the specific binding is made is stimulated and generates a light as a converted optical information in accordance with the stimulated energy. In the stimulable phosphor sheet are formed stimulable phosphor areas (areas containing stimulable phosphors) to be exposed to the radial ray. When the stimulable phosphor areas are overlapped with the reacted spot areas (the spot areas in which the specific binding reaction is made), the exposure of the some stumilable phosphor areas is made in radiation of the radial rays generated from the reacted spot areas. When an exiting light is illuminated on the some stimulable phosphor areas after the exposure, lights are generated from the some stimulable phosphor areas to form an image as a biochemical analysis data which is to be read.

In order to make the specific binding reaction, the shaking is usually made in the prior art. In the shaking method, a specific binding reaction solution (hereinafter reaction solution) and a biochemical analysis unit in which the probes are fixed are set in a reaction vessel, and the reaction vessel is shaken on a shaking stage. Thus the reaction solution containing the target is applied to and then penetrates into the spot areas. However, in the shaking method, as the examiner exchanges the reaction solution with his hands, there are following problems. Firstly, the equivalent penetration of the reaction solution is hard among the spot areas. Secondly, the penetration pressure into the spot areas is low, and the reaction is often made slowly, for example, at least for more than 10 hours, and for few days when it takes long time. Thirdly, not only for the different but also for the same examiner, it is hard to keep the supplied and the discharged reaction solution to the same temperature. Thus the experimental conditions change and the experiment cannot be replicated correctly.

Accordingly, instead of the shaking method, a flow through method is applied to the reaction method (See, WO 01/45843), in which a mechanical pressure of such as a piston, a pump and the like drives to flow the reaction solution from one side to another side in the spot area.

The reaction vessel to be used in the flow through method has a reaction chamber (hereinafter a chamber) in which the biochemical analysis unit is contained and the reaction solution is supplied. The chamber is provided with an inlet through which the reaction solution is supplied, and an outlet through which the reaction solution after flowing through the spot areas is discharged. The inlet and outlet are positioned so as to confront to a middle portion of the flow-through area in which the plural spot areas are arranged. The pump and the piston are driven to mechanically increase the pressure for feeding the reaction solution into the chamber. Thus the reaction solution flows into the chamber with increased feeding pressure, the pressure of the reaction solution for penetrating into the spot areas becomes more, and the reaction speed is increased. Further, with the mechanical drive of the piston, the pump and the like, the feed pressure is kept constant. Therefore the experimental condition does not become different.

On walls of the chamber is formed a taper which is curved towards the biochemical analysis unit such that the specific binding reaction solution supplied through the inlet can equivalently flow through all over the flow-through area.

However, in accordance with downsizing the chamber, the formation of the taper becomes difficult and the cost increases. Further, several steps of the reactions are sometimes made with use of the plural kinds of reaction solutions and the cleaning solution. In this case, since the physical properties of those solutions may change, it becomes hard that the reaction solution or the cleaning solution always equivalently flow through all over the flow-through area.

SUMMARY OF THE INVENTION

An object of the present invention is to provide a reaction method with use of a biochemical analysis unit in which a reaction solution and a cleaning solution equivalently flow through all over a flow-through area.

Another object of the present invention is to provide a reaction method in which the flow speed distribution through the flow-through area of the biochemical analysis unit is always reduced when the specific binding is made in plural steps with used of the reaction solution.

In order to achieve the above objects and other objects, in a method of performing a reaction with use of a biochemical analysis unit of the present invention, the biochemical analysis unit has a flow-through area in which plural spot area are arranged, and probed is spotted onto the plural spot areas. In the method of the present invention, the biochemical analysis unit is set into a reaction chamber, which is supplied with a solution containing a target as a test substance such that the solution may flow equivalently through the flow-through area. Then the specific bindings of the probe and the target in the spot areas are selectively performed when the solution flows equivalently through the flow-through area. A pressure loss is controlled from 1 kPa to 1 MPa when the solution flows equivalently through the flow-through area.

According to the chemical reaction with use of the biochemical analysis unit of the present invention, the probe as a reagent is fixed and the solution containing a target as a antibody is flowable in the spot area, and the biochemical analysis unit is set into a chamber in which the solution is supplied. The supplied solution flows the flow-through area. Thereby the target in the supplied solution penetrates into the spot areas, and the specific binding reaction of the target is selectively made with the probes in the spot areas. The pressure loss is from 1 kPa to 1 MPa when the solution flows through the flow-through area. Accordingly, the flow speed distribution of the solution all over the flow-through area is at most 5%. Thus the reaction is equivalently made in each spot area, and therefore the good analysis data can be obtained.

BRIEF DESCRIPTION OF THE DRAWINGS

The above objects and advantages of the present invention will become easily understood by one of ordinary skill in the art when the following detailed description would be read in connection with the accompanying drawings.

FIG. 6 is a sectional view of a reaction vessel;

PREFERRED EMBODIMENTS OF THE INVENTION

Figure 1:
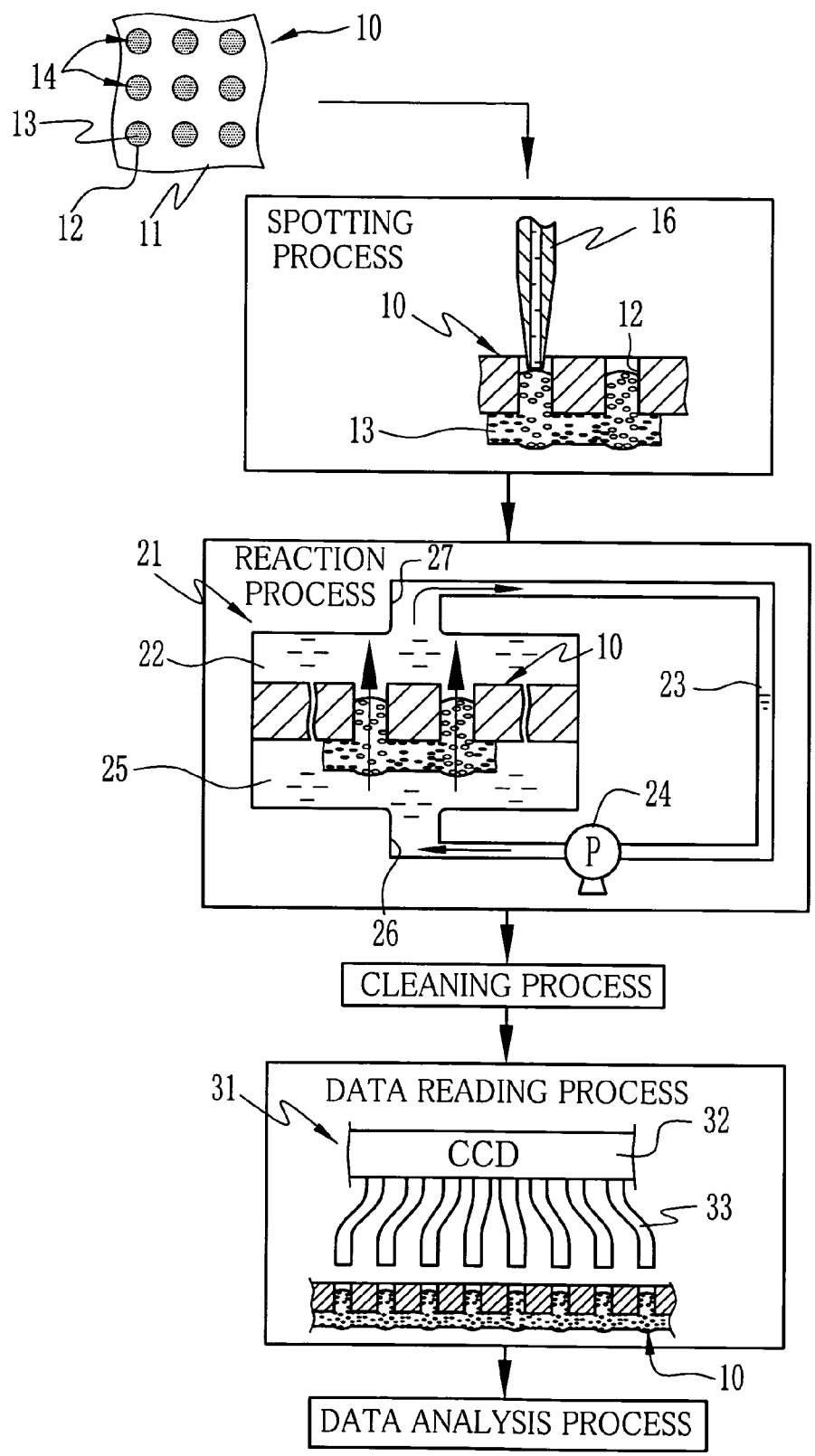
FIG. 1 is a flow chart illustrating all processes of biochemical analyzing method in which a biochemical analysis unit is used.

As shown in FIG. 1, a biochemical analyzing method in which a biochemical analysis unit 10 is used includes a spotting process, a reaction process, a cleaning process, a data reading process and a data analysis process. In the biochemical analysis unit 10, minute through holes 12 are formed in matrix-arrangement in the substrate 11, and a membrane 13 of the absorptive material is pressed into the through holes 12. Thus a spot area 14 is formed in each through hole 12, and the obtained biochemical analysis unit is a flow-through type.

In the spotting process, solutions containing different probes (hereinafter probe solutions) are spotted in the respective spot area 14 of the biochemical analysis unit 10 with use of a spotter. The spotter has spot pins 16 for spotting the prove solution, and a groove is formed on a tip of the spot pin 16. Plural kinds of the probe solutions which are dispensed on a well plate are sucked up and spotted in the spot area 14 by the spot pins 16. Thereafter, an UV-ray is irradiated on the spot areas 14 to fix the probe therein. Thus the biochemical analysis unit 10 in which the probes are fixed is placed in a biochemical analysis cartridge (hereinafter cartridge) 28 including a chamber 29.

In the reaction process, the specific binding reaction of the probe and a target as a test substance is made with use of a reactor 21. The reactor 21 is constructed of a reaction vessel 22, a circulating pipe 23 and a pump 24. In the reaction vessel 22, the biochemical analysis unit 10 is contained and a reaction solution 25 for performing the specific binding reaction is supplied. This embodiment is explained with use of chemifluorescent substances as a labeling substance, which generates a fluorescence in a chemical reaction. However, the labeling substance is not restricted in it.

The reaction solution 25 is prepared by a preparing device for the reaction solution 25. In the preparing device, a target to which the labeling substance is bound is dissolved to a solvent to prepare the reaction solution 25. The prepared reaction solution 25 is contained in a tank (not shown) provided on the reactor 21.

The reaction vessel 22 is provided with an inlet 26 for supplying the reaction solution 25 and an outlet 27 for discharging the reaction solution 25. The biochemical analysis unit 10 is set in the reaction vessel 22 such that one surface (a lower surface in this figure) may confront to the inlet 26 and another surface (upper surface in this figure) may confront to the outlet 27. The reaction solution 25 supplied into the reaction vessel 22 penetrates into the spot areas 14. In some of the spot areas 14, in which the complementary probes to the target are contained, the specific binding of the probe and the target is made. Then the reaction solution 25 flows through the spot areas 14 and is discharged through the outlet 27 from the reaction vessel 22.

The inlet 26 and the outlet 27 are connected to the circulating pipe 23, and the reaction solution 25 discharged from the reaction vessel 22 is fed through the pump 24 and the circulating pipe 23 to the reaction vessel 22 again. Further, when the reaction solution or the cleaning solution is supplied into or discharged from the reaction vessel 22, a supply pipe (not shown) and a discharge pipe (not shown) are respectively connected to the inlet 26 and the outlet 27. The inlet 26 and the outlet 27 are exchangeably connected to the supply pipe, the discharge pipe and the circulating pipe 23.

In the cleaning process after the reaction process, the biochemical analysis unit 10 is cleaned and the reaction solution is removed from other area than the spotting areas in which the specific binding is made. In this cleaning process, by use of the reactor 21, a cleaning solution is supplied instead of the reaction solution, and the cleaning is made in the flowage of the cleaning solution. Thus, the targets which have not made the specific binding reaction can be easily removed.

In order to obtain the better cleaning effects, it is preferable to have a so-called blocking agent penetrating into the biochemical analysis unit 10 previous to the reaction process. In this case, the targets which have not made the specific binding reaction can be easily removed, and thus the effect of the cleaning becomes better. In the penetration of the blocking agent into the biochemical analysis unit 10, it is preferable to use the reactor 21 in the same manner as for the cleaning solution. Since the cleaning solution and the blocking agent flows with a mechanical force in the same manner as the reaction solution, the cleaning effect becomes almost same between the different experiments. Accordingly, the analysis data is correctly obtained and excellent in replication property and quantification property.

After the cleaning process, the biochemical analysis unit 10 is sent to the data reading process, in which the data for biochemical analysis is photoelectrically read from the biochemical analysis unit 10 by a scanner 31. The scanner 31 includes a CCD image sensor 32 which receives a light generated from the labeling substances and photoelectrically converts into the light. In front of a receiving surface of the CCD image sensor 32, there is a light guide 33 for guiding the light to photosensitive elements of the CCD image sensor 32. The light guide 33 is constructed of optical fibers whose number is corresponding to that of the spot areas 14. One end of each optical fiber confronts to the receiving surface and another end to the corresponding spot area 14. Since the labeling substances remain in the some spot areas in which the specific binding reaction is made, the light is generated. Otherwise, the light is not generated in other spot areas in which the specific binding is not made. An image data formed as the result of the specific binding reaction in each spot area 14 is received by the CCD image sensor 32. In the data analyzing process, the image data is analyzed as the biochemical analysis data.

Figure 2:
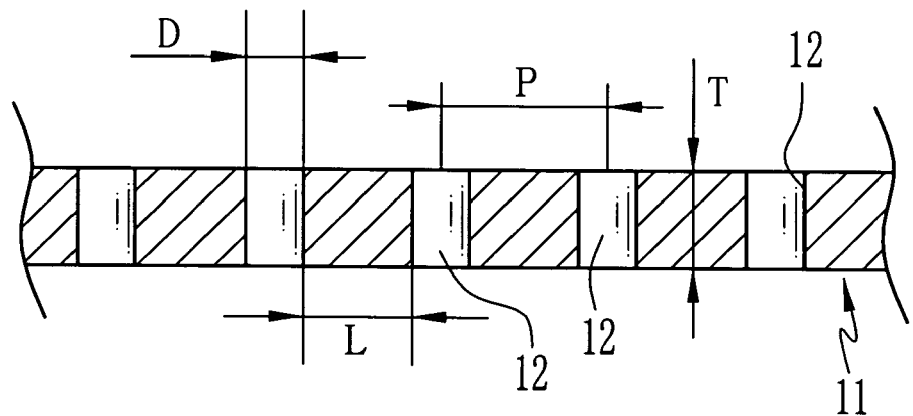
FIG. 2 is a sectional view of the biochemical analysis unit.
Figure 3:
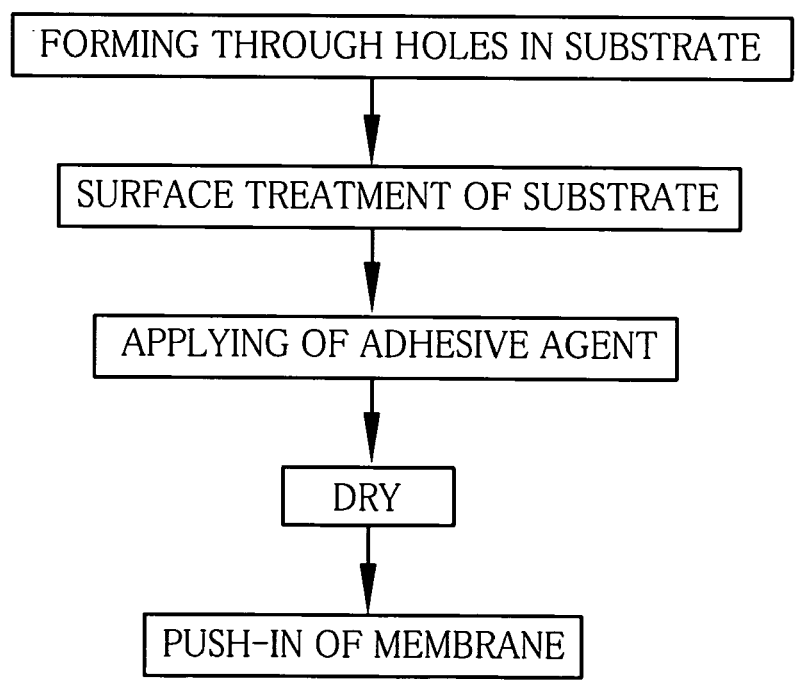
FIG. 3 is an explanatory view illustrating processes of producing the biochemical analysis unit.

FIGS. 2 to 4 are explanatory views of the biochemical analysis unit 10. The substrate 11 is formed of the materials which can decrease the light intensity so as to prevent the scattering of the light, for example metal, ceramics, plastics, and the like. When the light does not scatter, it is prevented to misunderstand that the light would be generated from the other areas than the some spot areas from which the light is generated. When the materials having high effect for decreasing the light intensity is used, the misunderstanding is prevented, and the analysis data having high reliability is obtained. The rate of decreasing the intensity of the light generated from the one spot area becomes preferably at most $1/5$, and especially at most $1/10$ in the neighboring spot area.

In FIG. 2, the thickness T of the substrate 11 is preferably in the range of 50 to 1000 μm, and especially in the range of 100 to 500 μm. As the metals, there are copper, silver, gold, zinc, plumbum, aluminum, titanium, tin, chromium, iron, nickel, cobalt, tantalum and the like. Further, alloys, such as stainless, brass and the like, may be used. However, the metals are not restricted in them. Furthermore, as the ceramics, there are alumina, zirconia and the like. However, the materials to be used are not restricted in them.

As the plastics, there are olefins (for example, polyethylene, polypropylene, and the like), polystyrene, acryl resin (for example, polymethylmethacrylate, and the like), polymers containing chlorine (for example, polyvinyl chloride, polyvinylidene chloride and the like), polymers containing fluorine (for example, polychlorotrifluoroethylene, and the like), polycarbonates, polyesters, (for example, polyethylene naphthalate, polyethylene telephthalate and the like), polyamide (for example nylon-6, nylon-66 and the like), polyimide, polysulfonate, polyphenylen sulfide, silicon resins (for example, polydiphenyl cyclohexane and the like), phenol resins (for example, noborac and the like), epoxy resins, polyurethane, celluloses (for example, cellulose acetate, nitrocellulose and the like), and the like. Further, there are copolymers (for example butadiene-cellulose copolymer, and the like). Furthermore the above polymers may be blended. However, the sorts of the plastics are not restricted in them.

It is preferable to use the plastics as the materials of the substrate, since the through holes are easily formed. However, in this case, the light intensity is hardly decreased. In order to decrease the light intensity moreover, preferably, metal oxide particles or glass fiber particles are added to the plastics, and dispersed therein. As the metal oxide particles, there are silicon dioxide, alumina, titanium dioxide, iron oxide, cupper oxide and the like. However, the sorts of the metal oxide are not restricted in them.

A method of forming the through holes 12 are a punching method, pulse discharging method, etching method, and methods in which a laser beam (exima laser and YAG laser) is applied to the substrate. However, the method of forming the through holes is not restricted in them, and selected depending on the material of the substrate.

In order to make the density of the through holes 12 higher, the area of a opening of the each through hole is preferably less than 5 mm$^2$, particularly less than 1 mm$^2$, and especially less than 0.3 mm$^2$, more especially less than 0.01 mm$^2$, and most especially less than 0.001 mm$^2$. Further, when the through hole has a nearly circular shape, the diameter thereof is preferably 200 μm to 300 μm.

A arrangement pitch P of the through holes 12 (a distance of centers between neighboring through holes 12) is preferably 50 μm to 3000 μm, and a length of the nearest edges between the neighboring through holes is preferably 10 μm to 1500 μm. Further, the number of the through holes 12 in a unit area is preferably at least 10/cm$^2$, particularly at least 100/cm$^2$, especially at least 500/cm$^2$, most especially from 1000/cm$^2$ to 10000/cm$^2$.

FIG. 3 is a producing process of a biochemical analysis unit 10. The through holes 12 are formed in the substrate 11. In order to make the cleaning effect higher, a surface treatment is made on the substrate 11. When metals and alloys (for example stainless and the like) are used as the materials of the substrate 11, the surface treatment is made in at least one of corona discharging method, plasma discharging method and an anodic oxidization method. In the surface treatment, a surface treatment layer is formed on the substrate 11, and is a layer of metal oxide having hydrophilic property since containing carbonyl groups and carboxyl groups.

After the surface treatment, an adhesive agent is applied to a surface of the substrate 11, on which the membrane 13 is pressed for the insertion into the through holes 12. The method of applying the adhesive agent is not restricted. However, it may be performed by a roller coating, a wire bar coating, a dip coating, a blade coating, an air knife coating or the like. As the adhesive agents, there are styrene-butadiene rubber and acrylonitril-butadiene rubber. However, it is not restricted in them. Note that the excessive adhesive agent is scratched and removed by the blade, or may be removed with use of a laser beam for preventing the generation of the impurities in the following process. Note that the processes of the surface treatment of the substrate and the application of the adhesive agent can be omitted, when the biochemical analysis unit used in the present invention is produced.

After the application of the adhesive agents, the membrane 13 is pressed into the through holes 12. As the membrane 13, there are porous materials and fiber materials. Note that the porous materials and the fiber materials are used simultaneously. The membrane 13 used in the present invention may be one of the porous materials (organic, inorganic porous materials or mixture thereof), the fiber materials (organic or inorganic fiber materials). Further these may be mixed. The thickness of the membrane 13 is not restricted especially. However, it may be in the range of 100 µm to 200 µm (0.10 mm to 0.20 mm). The void ratio in volume is preferably from 55% to 90%, and the average pore diameter of pores constructing a void is preferably in the range of 0.1 µm to 10 µm. Further, a void ratio C in volume is a percentage of a total volume of the voids to the appearance volume of the absorptive materials.

The sorts of the organic porous materials are not restricted especially. However, they are preferably polymers, for example, cellulose derivatives (for example, nitro cellulose, regenerated cellulose, cellulose acetate, cellulose acetate butyrate, and the like), aliphatic polyamides (for example, nylon-6, nylon-66, nylon 4,10, and the like), polyolefines (for example, polyethylene, polypropyrene), polymers containing chlorinate (for example, polyvinyl chloride, polyvinylidene chloride and the like), fluorine resins (for example, polyvinylidene floride, polytetrafluoride and the like), polycarbonate, polysulfone, alginic acid, and derivatives thereof (for example, calcium alginate, ion complex of alginic acid/polylysine, and the like) collagen, and the like. Further, the copolymer or the complexes (or mixture) of these polymers may be used. Note that porous nylon is preferably used in view of the water absorbing properties in the present invention.

The sorts of the inorganic porous materials are not restricted. However, they are preferably metal (for example, platinum, gold, iron, silver, nickel, aluminum, and the like), metal oxide (for example, alumina, silica, titania, zeolite, and the like), salts of metals (hydroxyapatite, calcium sulfate and the like) complexes of them, and the like. Further, porous carbon materials (activated carbon and the like) may be used.

Further, organic fiber materials and the inorganic fiber materials are not restricted in them. However, as the organic fiber materials, the cellulose derivatives, aliphatic polyamides and the like can be used, and as the inorganic fiber materials, glass fiber and metal fiber can be used. Note that in order to increase the strength of the membrane 13, the fiber materials insoluble to the solvent can be used, while the porous materials can be dissolve to the solvent.

Figure 4A:
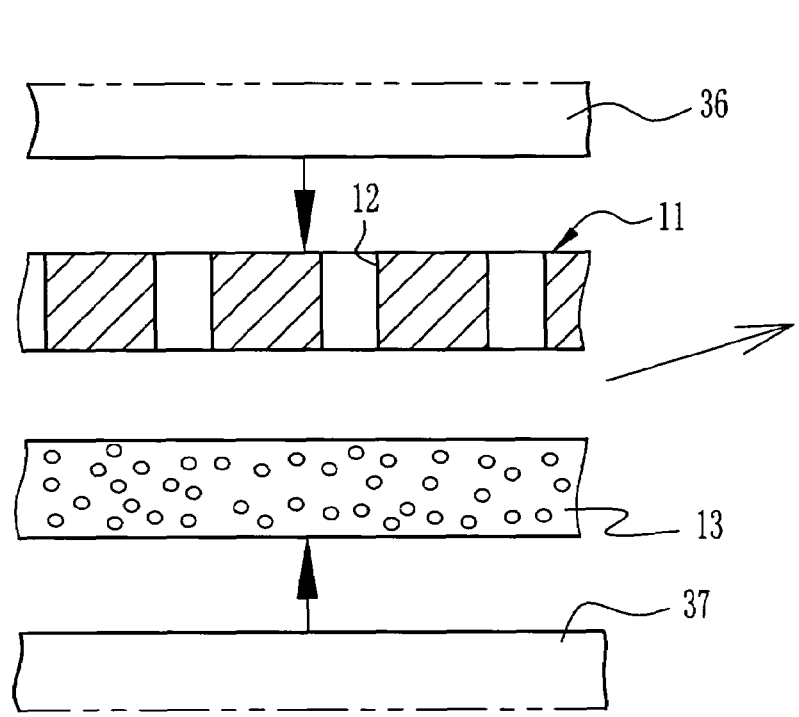
FIG. 4A is an explanatory view for explaining a method of producing the biochemical analysis unit.
Figure 4B:
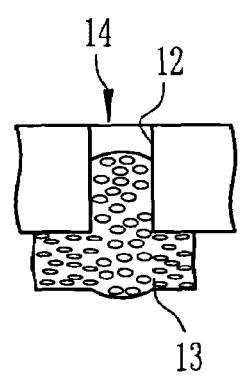
FIG. 4B is a sectional view of the biochemical analysis unit.

In FIGS. 4A,4B, the pressing of the membrane 13 is intermittently made from up and down sides by press plates 36,37 in the situation that the substrate 11 and the membrane 13 are superimposed. Note that when the organic porous or fiber materials are used as the membrane 13, the press plate 36 (in upper side in this figure) is heated so as to increase the temperature of the substrate 11. Thus the membrane 13 becomes softened, and easily pressed into the through holes 12 to form the spot area 14. Further, a roller may be used instead of the press plates.

Figure 5A:
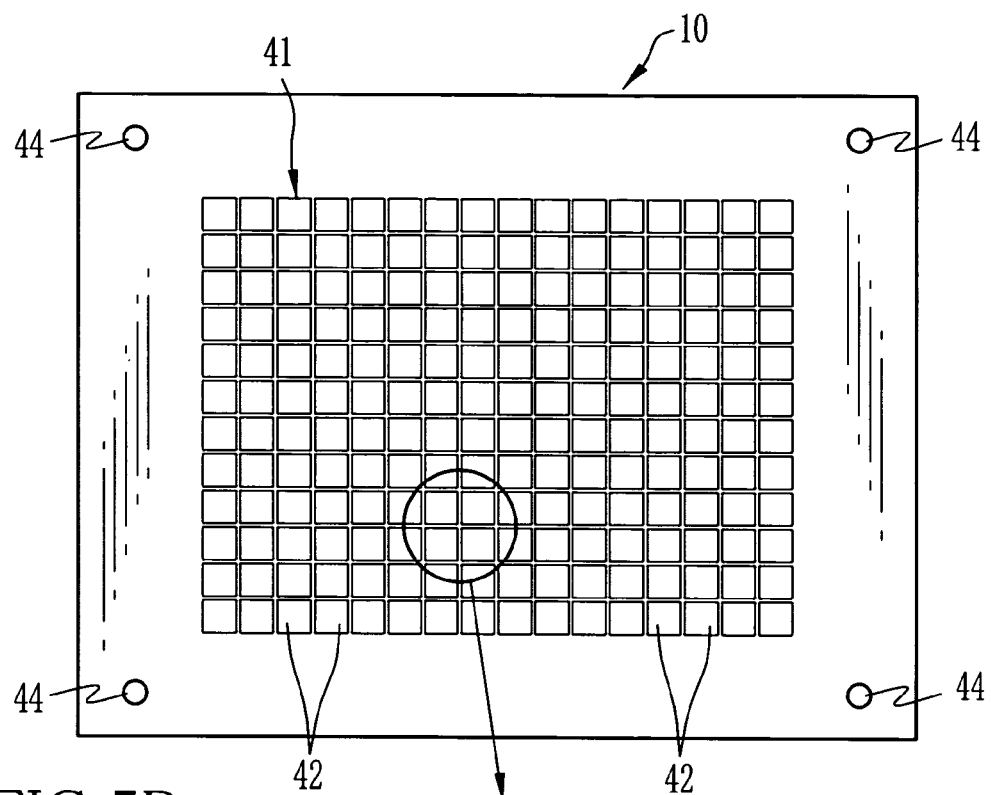
FIG. 5A is a plan view of a biochemical analysis unit.
Figure 5B:
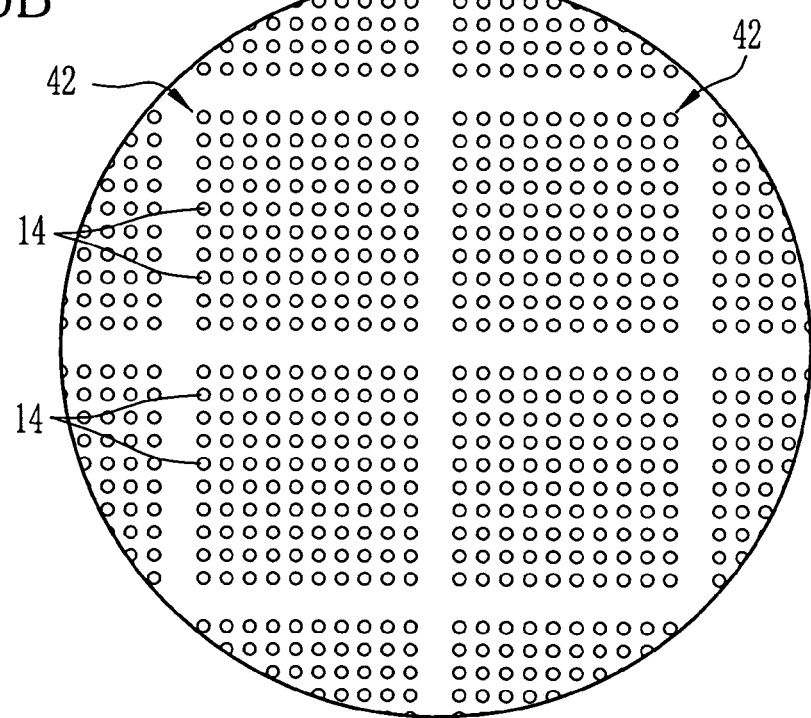
FIG. 5B is an exploded plan view of a biochemical analysis unit.

FIGS. 5A&5B are plan views of the biochemical analysis unit 10 used in the present invention. A flow-through area 41 in which the spot areas 14 are arranged has a generally rectangular shape, and is regularly sectioned into rectangular blocks in which a predetermined number of the spot areas 14 is formed. The size of the substrate 11 is, for example, 70 mm in length and 90 mm in width. Size of each block 42 is about a radius of 4 mm. The blocks are matrix-likely arranged, and the number thereof in length is 12, and that in width is 16. The features of the flow-through areas (namely size and the number of the block, and the size and the pitch of the arrangement of each spot area 14) are determined, corresponding to the feature of the CCD image sensor 32. Positioning holes 44 are used for an attachment of the biochemical analysis unit 10 to the cartridge 28. Note that the substrate 11 is separated into the blocks having the predetermined number of the spot areas 14 in this embodiment. However this sectioning may not be made. For example, the spot areas 14 may be arranged all over the flow-through area 41.

FIG. 6 is a sectional view of the reaction vessel 22 in which the biochemical analysis unit 10 is loaded. The reaction vessel 22 is constructed of an upper part 51 and a lower part 52. Recess 51a,52a are respectively formed on a bottom of the upper part 51 and a top of the lower part 52 in this figure. When the upper and lower parts 51,52 are superimposed, the recesses 51a, 52a are combined to construct the chamber 53. Around the recesses 51a, 52a are formed retainers 56a, 56b which nip the biochemical analysis unit 10 for retaining it. In the chamber 53, the biochemical analysis unit 10 is contained and the reaction solution 25 is supplied. Further, it is preferable to provide a heater 54 for adjusting a temperature of the reaction solution 25 in the chamber 53. The adjustment of the temperature makes a regulation of the sharing viscosity and the reaction period possible.

The inlet 26 and the outlet 27 are provided in central areas of the respective recesses 51a,52a, and disposed so as to confront to a middle portion of the flow-through area 41, when the biochemical analysis unit 10 is set therein. Further, a height H from the inlet 26 to the biochemical analysis unit 10 is preferably in the range of 0.02 mm to 20 mm, and particularly preferably 0.2 mm to 2 mm.

Processes of a reaction in an indirect labeling method with use of the above structure will be explained in the followings. At first, reaction solution containing antigens is supplied into the chamber so as to make a specific binding reaction to the probe. Thus in the spot area in which the specific biding reaction is made, the antigen remains. Thereafter, the cleaning is made with use of the cleaning solution to remove the reaction solution. Thereafter supplied into the chamber is an antigen solution containing an enzyme-labeled antibody which makes the specific binding to the antigen. In the spot area in which the antigen remains, the enzyme labeled antibody which binds to the antigen will remain. Thereafter, the cleaning is made with use of an antibody cleaning solution, and thus the other enzyme labeled antibody which does not bind to the antigen is removed. After this cleaning, the enzyme labeling antibody and the chemiluminescent substrate as the labeling substance are put into a chemiluminescent reaction. As the labeling substance, for example, there are chemiluminescent substrates, such as CDP-star (trademark) and the like. The enzyme-labeling antibody decomposes the chemiluminescent substrate. In the decomposition, the chemiluminescent substrates generate a light.

Figure 7:
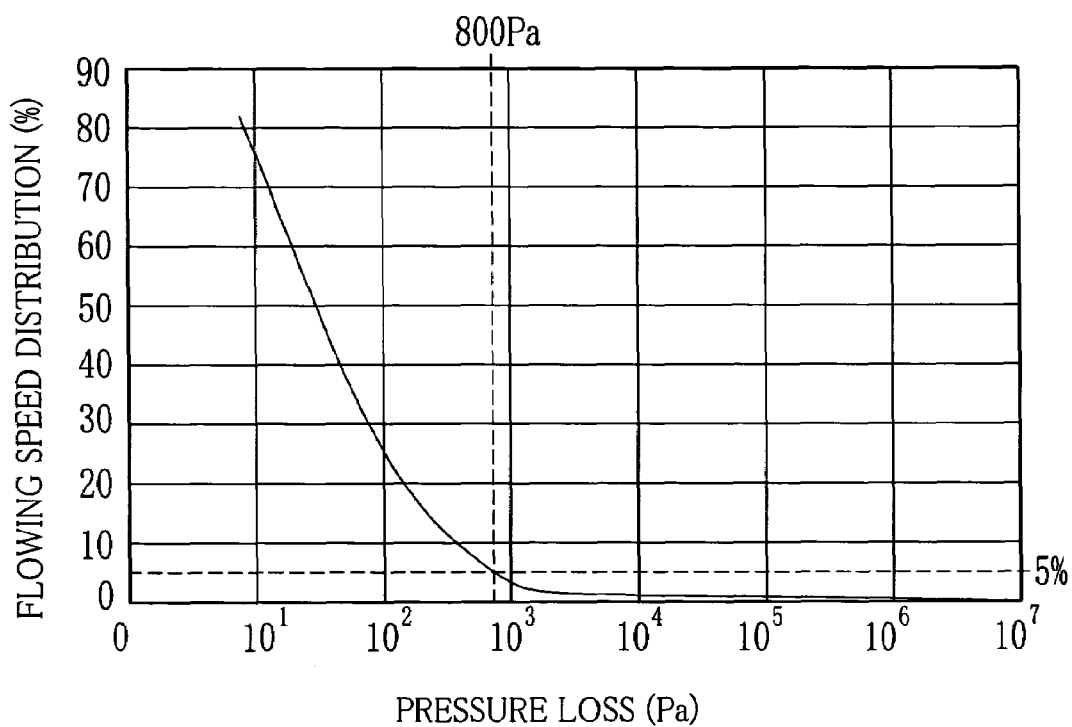
FIG. 7 is a graph explaining a relation between a flow speed distribution and a pressure loss through a flow-through area.

FIG. 7 is a graph illustrating a relation between a pressure loss and a flow speed distribution all over the flow-through area. The pressure loss occurs when each solution passes through the flow-through area. In the present invention, the distribution of the signals in the data reading process is in ±20%. Furthermore the allowable value of the flow speed distribution is preferably at most 5%. In this case, FIG. 7 teaches that the pressure loss may be at least 800 Pa, and preferably at least 1 kPa. When the pressure loss of the solution flowing through the flow-through area 41 is high, the solutions supplied from the inlet 26 (for example, the reaction solution, the cleaning solution and the like) flow through all over the flow-through area 41. Therefore the higher pressure loss is preferable since the flow speed distribution decreases.

However, when the pressure loss is too high, it is necessary to make a pressure tightness of all parts of the reactor 21 higher, and to increase the pump's capacity for feeding the solution. These cause the increase of cost. Accordingly, the pressure loss is preferably at most 1 MPa in the present invention.

In order to regulate the pressure loss in the range of 1 kPa to 1 MPa, the adjustments of the following conditions are made.
(1) a flow speed of the solution flowing through the flow-through area is from 0.1 mm/s to 20 mm/s,
(2) a void ratio of the membrane in the flow-through area is from 55% to 90%,
(3) an average pore diameter of the membrane is from 0.1 μm to 10 μm,
(4) a temperature of the solution just before the supply into the chamber is from 25° C. to 80° C.,
(5) a height from the inlet of the chamber for supplying the solution to the biochemical analysis unit is from 0.02 mm to 20 mm,
(6) an averaged temperature of the solution in the chamber is from 25° C. to 80° C.

Accordingly, the solution flows almost equivalently in the flow-through area without special manufacturing to the chamber. Note that a reaction vessel including the chamber of taper-like form may be used.

As the reaction in the present invention, in which the probe as the reagent selectively makes the specific binding to the target as the test substance, there are a ligand receptor reaction, an antigen-antibody reaction, a hybridization reaction and the like.

An example of the method of performing the reaction with use of the biochemical analysis unit for antigen-antibody reaction will be explained in detail. However, the present invention is not restricted in the following. In the spotting process, different probes were spotted onto and fixed to the spot areas 14 of the biochemical analysis unit 10. Note that the average pore diameter of the membrane 13 which was filled in the spot area 14 was 0.45 μm, while it is preferably from 0.1 μm to 10 μm, as described above. In the reaction process, the biochemical analysis unit 10 was set in the reaction vessel 22. Feed pipes were connected to the inlet 26 and the outlet 27, and the reaction solution 25 was supplied from a tank (not shown) into the chamber 53. Then the chamber 53 was filled with the reaction solution 25 to extract an air, and thereafter the feed switch of the feed pipes was set to feed the reaction solution to the circulating pipe 23, such that the circulating pipe 23 may be connected to the inlet 26 and the outlet 27. Note that the height H of the biochemical analysis unit 10 from the inlet 26 was set to 2 mm.

When the hybridization is designated, it is preferable to use a buffer solution which keeps the pH value almost constant for proceeding the specific binding. In this embodiment, a phosphoric acid buffer solution was used as the reaction solution 25. The temperature of the reaction solution 25 was controlled to 68° C., and the reaction solution 25 was supplied into the chamber 53. The temperature of the chamber 53 was controlled to 68° C. by the heater 54. The sharing viscosity of the reaction solution as the hybridization solution at 68° C. was 0.73 mPa·s, and the surface tension of it was 31.5 mN/m. The flow speed of the reaction solution 25 flowing though the flow-through area 41 was 1.77 mm/s, and the pressure loss was about 80 kPa.

After the hybridization, the cleaning for removing the reaction solution 25 as the hybridization solution was made. The cleaning solution was supplied into the chamber 53 with use of the pump 24. Thereby the temperature of the chamber 53 was adjusted to 68° C. Thereafter the blocking process was made, and the blocking agent was supplied into the chamber 53 with use of the pump 24. Thereby the temperature of the chamber 53 was adjusted to 37° C.

Then the antigen-antibody reaction was made. The antigen-antibody reaction solution was supplied into the chamber 53 with use of the pump 24. The temperature of the chamber 53 was adjusted to 37° C. Further, the cleaning for removing the antigen-antibody reaction solution was made. The cleaning solution for the antigen-antibody solution was supplied into the chamber 53 with use of the pump 24. Thereby the temperature of the chamber 53 was adjusted to 37° C. Then the chemiluminescent reaction process was made. The chemiluminescent reaction solution was supplied into the chamber 53 with use of the pump 24. Thereby the temperature of the chamber 53 was adjusted to 37° C.

The pressure loss of the solution flowing through all over the flow-through area 41 was from about 10 kPa to 80 kPa. Therefore, the reaction and the cleaning were equivalently made in all the spot areas to obtain the good analysis data.

Various changes and modifications are possible in the present invention and may be understood to be within the present invention.

What is claimed is:

1. A method of performing a reaction using a biochemical analysis unit having a flow-through area in which plural spot areas are arranged comprising:
    setting the biochemical analysis unit into a chamber;
    supplying the chamber with a solution containing a target as a test substance, wherein the solution flows through a flow-through area;
    performing specific binding of a probe and the target in plural spot areas when the solution flows through the flow-through area; and
    wherein a pressure loss of the solution is controlled from 1 kPa to 1 MPa to allow the solution to flow equivalently through the flow-through area, and the pressure loss is controlled from 1 kPa to 1 MPa by the following conditions:
    a flow speed from 0.1 mm/s to 20 mm/s of the solution containing a target flowing equivalently through the flow-through area, and
    a temperature from 25° C. to 80° C. of the solution containing a target when the solution is supplied into the chamber.

2. The method of claim 1, wherein the flow-through area has a void ratio of a membrane from 55% to 90%.

3. The method of claim 2, wherein the membrane has an average pore diameter from 0.1 μm to 10 μm.

4. The method of claim 3, wherein the biochemical analysis unit has a height measured from an inlet to the biochemical analysis unit chamber for supplying the solution from 0.02 mm to 20 mm.

5. The method of claim 4, wherein the solution containing a target has an average temperature in the chamber from 25° C. to 80° C.

* * * * *